US007868191B2

(12) United States Patent
Aassveen

(10) Patent No.: US 7,868,191 B2
(45) Date of Patent: Jan. 11, 2011

(54) PREPARATION AND PURIFICATION OF MUPIROCIN CALCIUM

(75) Inventor: Lene Aassveen, Oslo (NO)

(73) Assignee: Xellia Pharmaceuticals ApS, Copenhagen (DK)

( * ) Notice: Subject to any disclaimer, the term of this patent is extended or adjusted under 35 U.S.C. 154(b) by 0 days.

(21) Appl. No.: 12/310,216

(22) PCT Filed: Aug. 29, 2007

(86) PCT No.: PCT/EP2007/007547

§ 371 (c)(1),
(2), (4) Date: Feb. 17, 2009

(87) PCT Pub. No.: WO2008/025534

PCT Pub. Date: Mar. 6, 2008

(65) Prior Publication Data

US 2009/0240071 A1 Sep. 24, 2009

(30) Foreign Application Priority Data

Aug. 30, 2006 (GB) .................................. 0617069.0

(51) Int. Cl.
*C07D 407/06* (2006.01)
(52) U.S. Cl. .................. 549/414; 549/417; 549/561
(58) Field of Classification Search ................ 549/414, 549/417, 561
See application file for complete search history.

(56) References Cited

U.S. PATENT DOCUMENTS

| 3,977,943 A | 8/1976 | Barrow et al. |
| 4,071,536 A | 1/1978 | Barrow et al. |
| 4,222,942 A | 9/1980 | O'Hanlon et al. |
| 4,289,703 A | 9/1981 | Barrow et al. |
| 5,191,093 A | 3/1993 | Baker et al. |
| 6,245,921 B1 | 6/2001 | Barta et al. |
| 2005/0272768 A1 | 12/2005 | Szabo et al. |

FOREIGN PATENT DOCUMENTS

| BE | 870855 A1 | 3/1979 |
| DE | 2227739 A1 | 1/1973 |
| WO | WO-03/065975 A2 | 8/2003 |
| WO | WO-2006/087237 A1 | 8/2006 |
| WO | WO-2008/025534 A1 | 3/2008 |

OTHER PUBLICATIONS

"International Application Serial No. PCT/EP2007/007547, International Preliminary Report on Patentability completed Jul. 16, 2008", 6 pgs.
"International Application Serial No. PCT/EP2007/007547, International Search Report mailed Dec. 18, 2007", 5 pgs.
"International Application Serial No. PCT/EP2007/007547, Response filed Feb. 13, 2008 to the Written Opinion and International Search Report mailed Dec. 18, 2007", 5 pgs.
"International Application Serial No. PCT/EP2007/007547, Written Opinion mailed Dec. 18, 2007", 6 pgs.

*Primary Examiner*—Janet L Andres
*Assistant Examiner*—David E Gallis
(74) *Attorney, Agent, or Firm*—Schwegman, Lundberg & Woessner, P.A.

(57) ABSTRACT

The present invention relates to methods for the preparation and purification of mupirocin calcium. The process comprises adsorbing mupirocin to a hydrophobic adsorbent resin, exposing the bound mupirocin to a calcium-containing solution, washing impurities from the resin and eluting purified mupirocin calcium from the resin.

19 Claims, No Drawings

PREPARATION AND PURIFICATION OF MUPIROCIN CALCIUM

FIELD OF THE INVENTION

The present invention relates to improved processes for the preparation and purification of mupirocin calcium.

BACKGROUND

Mupirocin is an antibacterial agent produced as pseudomonic acid A by fermentation of *Pseudomonas fluorescens*. It is active against susceptible strains of *Staphylococcus aureus* and *Streptococcus pyogenes*, and is typically utilized as a topical solution. Mupirocin has the molecular formula $C_{26}H_{44}O_9$ (molecular weight=500.63) and the chemical name (E)-(2S,3R,4R,5S)-5-[(2S,3S,4S,5S)-2,3-Epoxy-5-hydroxy-4-methylhexyl]tetra-hydro-3,4-dihydroxy-(beta)-methyl-2H-pyran-2-crotonic acid, ester with 9-hydroxynonanoic acid. The chemical structure of mupirocin is shown below:

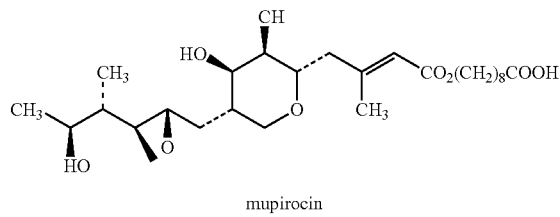

mupirocin

The calcium salt of pseudomonic acid A, mupirocin calcium or calcium pseudomonate, provides higher thermal stability, especially in crystalline state (U.S. Pat. No. 5,191,093). This stability is particularly favorable in formulations that involve higher temperatures.

Several methods for purifying mupirocin and derivatives thereof are known in the art. For example, U.S. Pat. No. 5,191,093 describes a process for preparing crystalline calcium pseudomonate or a hydrate thereof which process comprises reacting pseudomonate ions with calcium ions in solution in an aqueous solvent, recovering a crystalline calcium pseudomonate hydrate from the solution and therafter optionally removing water of crystallization. The method provides a simple means of converting mupirocin acid to the calcium salt. However, the purification effect of the operation is limited and a pure starting material is required to obtain a product that is acceptable for pharmaceutical use. U.S. Pat. No. 3,977,943 relates to purification from culture broth by chromatography on Amberlite XAD-2 polystyrene resin and elution using a series of low molecular weight acids. German patent 2227739 and U.S. Pat. No. 4,289,703 relate to a purification process using sodium barium and methyl isobutyl ketone (MIBK). Belgian Pat. No. 870,855 relates to a process involving extraction of mupirocin from fermentation broth using MIBK and sodium hydrogen carbonate and crystallization from a MIBK-n-heptane mixture. U.S. Pat. No. 4,222,942 relates to a process involving extraction in a polar water immiscible organic solvent, and dilution in a non-polar solvent to effect crystallization. U.S. Pat. No. 6,254,921 relates to a process of extraction using a chlorinated aliphatic hydrocarbon or isobutyl acetate and evaporation of organic solvent.

Like U.S. Pat. No. 5,191,093, WO03/065975 A2 provides a process for preparing mupirocin calcium from mupirocin in a two phase system by using an organic carboxylate and isolating solid mupirocin calcium from the aqueous phase, or by first precipitating amorphous mupirocin calcium from a $C_1$-$C_4$ alcohol, and then convert the amorphous product to the crystalline form.

Several methods for purification of Mupirocin Acid are known in the art, e.g. U.S. Pat. No. 4,222,942 (as noted above), these methods generally relates to partitioning of mupirocin in acidified/alkaline aqueous solution and polar water immiscible organic solvents such as methyl isobutyl ketone (MIBK) and isobutyl acetatate, followed by crystallization from an organic solvent such as MIBK. According to U.S. Pat. No. 4,289,703 A, soluble barium salts are added to the fermentation broth, then the microorganism cells with the insoluble inactive agents are separated by centrifugation and finally the antibiotics are extracted by MIBK. The antibiotics are then removed from the methyl isobutyl ketone extract by alkaline water and the resulting alkaline aqueous extract is cleaned by re-extraction with MIBK. The crude product obtained is subjected to chromatography and an ester derivative is prepared from the pseudomonic acid antibiotic complex and purified with preparative thin layer chromatography. The acid form of the pure antibiotic is obtained by hydrolysis.

These methods involve high volumes of hazardous agents, and there still remains a need for a novel method for the manufacture of mupirocin calcium, which combines purification and conversion of the mupirocin to the calcium salt. Such a novel process would lead to a shorter production process, and as such be commercially and environmentally more attractive.

There is a need in the art for more efficient processes for producing purified preparations of mupirocin derivatives, such as mupirocin calcium. Such processes and products produced thereby are provided herein, as discussed below.

SUMMARY

The present invention relates to methods for preparation and purification of mupirocin calcium. In one embodiment, the process comprises adsorbing a cell-free preparation of mupirocin (soluble salt or acid, preferably in the form of a soluble salt e.g. pseudomonate) to a solid support, exposing the bound mupirocin to a calcium-containing solution, washing impurities from the solid support, and eluting purified mupirocin calcium from the solid support. Also provided are preparations of mupirocin calcium prepared and purified using such methods.

In another embodiment, a cell-free preparation of mupirocin is prepared, following adsorption of a pseudomonate to a solid support. The bound pseudomonate is thereafter contacted with a calcium-containing solution and mupirocin calcium is formed on the solid support. Impurities are thereafter washed out followed by selective elution of the target molecule from the solid support. Surprisingly, a complete salt swap to calcium is achieved on the adsorbed pseudomonate and the correct molecular equivalency between mupirocin and calcium is obtained.

The method provides high purification efficiency due to selective removal of impurities during processing.

DETAILED DESCRIPTION

Mupirocin is an antibacterial agent produced as pseudomonic acid A by fermentation of *Pseudomonas fluorescens*. It is active against susceptible strains of *Staphylococcus aureus* and *Streptococcus pyogenes*, and is typically utilized as a topical solution. Mupirocin has the molecular formula $C_{26}H_{44}O_9$ (molecular weight=500.63) and the chemical name (E)-(2S,3R,4R,5S)-5-[(2S,3S,4S,5S)-2,3-Epoxy-5-hydroxy-4-methylhexyl]tetra-hydro-3,4-dihydroxy-(beta)-methyl-2H-pyran-2-crotonic acid, ester with 9-hydroxynonanoic acid. The chemical structure of mupirocin is shown below:

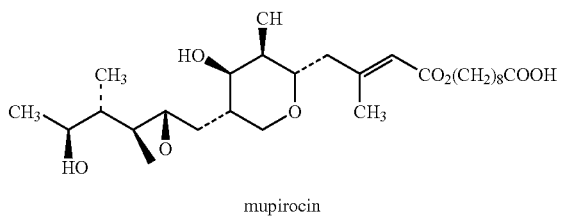

mupirocin

As used herein, the term "mupirocin" may refer to pseudomonic acid A, mupirocin acid, mupirocin calcium, pseudomonate, or any mupirocin derivate. The processes described herein are particularly useful for preparing and purifying mupirocin calcium. The processes described herein are particularly useful for preparing and purifying mupirocin calcium.

Within this application, a method for preparation of mupirocin calcium comprising adsorbing mupirocin (in the form of a soluble salt or acid, preferably a soluble salt e.g. pseudomonate) to a solid support, typically a hydrophobic adsorbent resin, exposing the bound mupirocin to a calcium-containing solution, washing impurities from the solid support and eluting purified mupirocin calcium from the solid support, is provided.

One method comprises adsorption of a pseudomonate to a solid support, typically an adsorbent resin, contacting the bound pseudomonate with a calcium-containing solution, washing out impurities, and eluting purified mupirocin calcium from the solid support. The eluted product can thereafter be crystallized and pure mupirocin calcium isolated by a method known in the art, e.g. as described in U.S. Pat. No. 5,191,093.

A cell-free preparation of mupirocin is utilized. This is prepared by fermenting a mupirocin-producing culture of *Pseudomonas fluorescens*, obtaining the fermentation broth thereof, and removing the biomass (clarifying the broth) by filtration. The pH of the solution is adjusted so as to assure that all mupirocin is deprotonated, i.e. a pseudomonate. Ammonium sulfate may be added to the mupirocin preparation prior to adsorption to the solid support in order to increase the hydrophobic interactions between the molecule and the adsorbent, and thereby increase the binding capacity of the resin for the pseudomonate.

A method for preparing a mupirocin preparation is described in U.S. Pat. No. 3,977,943. Briefly, a suitable strain of *Pseudomonas fluorescens*, such as strain NCIB 10586, is grown in submerged culture at 30° C. in a medium containing corn steep liquor and glucose in a basic salts solution for approximately 24 hours. Several methods of preparing the fermentation broth are known in the art and would be suitable for use herein.

A solid support may be any material capable of reversibly adsorbing to mupirocin acid. The solid support is a material to which mupirocin binds through hydrophobic interactions in such a way that the acid group of mupirocin is available for binding to other agents, compounds, or moieties such as calcium ions. Another important characteristic of the solid support is that binding of mupirocin to the support is reversible at the option of the skilled artisan. In certain embodiments, the solid support is a resin and in certain others it is a hydrophobic adsorbent resin. Suitable adsorbent resins include but are not limited to modified agaroses, modified silica, polystyrenic or acrylic/metacrylic materials. Examples of adsorbent resins include, but are not limited to, the acrylic adsorbents XAD7HP® (Rohm & Haas) or HP2MG® (Diaion), and the polystyrene divinylbenzene adsorbents XAD1600®, XAD4® (both being available from Rohm and Haas) or HP40® (Diaion).

Suitable hydrophobic adsorbent resins include but are not limited to modified silica, polystyrene or acrylic materials and include, for example, the acrylic adsorbent XAD7HP (Rohm & Haas) or HP2MG (Diaion), and the polystyrene divinylbenzene adsorbents XAD1600, XAD4.

In a first method, mupirocin (e.g pseudomonate or mupirocin acid, preferable pseudomonate) is adsorbed to a solid support, exposed to a calcium-containing agent and eluted from the column, thus providing a solution of mupirocin calcium. In preferred embodiments, the calcium-containing agent is calcium-based soluble salt. Exemplary calcium-containing agents include but are not limited to calcium chloride, calcium acetate, calcium nitrate and calcium propionate. Elution may be carried out using an organic solvent for example methanol. Elution may be carried out using other suitable agents which include but are not limited to ethanol, isopropanol and acetonitrile or any mixtures of these, including aqueous mixtures.

The methods described above also include the addition of ammonium sulfate preparation of mupirocin prior to adsorption to the solid support. Ammonium sulfate is added prior to adsorption to increase the hydrophobic interactions between the mupirocin molecule and the adsorbent, and thereby increase the binding capacity. In other embodiments, the preparation of mupirocin acid is purified mupirocin.

The methods described above are useful in preparing purified mupirocin calcium. In certain embodiments, purified mupirocin calcium is purified to at least 50%; at least 65%; at least 70%; at least 80%; or at least 90%.

Mupirocin calcium purified using the methods described herein may be prepared as a composition for use in treating mammals using standard techniques in the art. The composition(s) may be processed in accordance with conventional methods of pharmacy to produce medicinal agents for administration to patients (i.e., a "pharmaceutical composition"), including humans and other mammals. The pharmaceutical composition is preferably made in the form of a dosage unit containing a given amount of purified mupirocin, alone or in combination with another active agent, typically in conjunction with a pharmaceutically acceptable carrier. The term "pharmaceutically acceptable carrier" refers to one or more formulation materials suitable for accomplishing or enhancing the delivery of mupirocin as a pharmaceutical composition. The pharmaceutical compositions may also be subjected to conventional pharmaceutical operations such as sterilization and/or may contain conventional adjuvants, such as preservatives, stabilizers, wetting agents, emulsifiers, buffers, and the like.

A suitable daily dose for a human or other mammal may vary widely depending on the condition of the patient and other factors, but can be determined using routine methods known by those skilled in the art. For topical administration, a suitable topical dose of a composition may be administered one to four, and preferably two or three times daily. The dose may also be administered with intervening days during which no dose is applied. Suitable compositions may comprise from 0.001% to 10%, less than 5%, 1-2%, or 0.1-1% mupirocin of the formulation. Formulations suitable for topical administration include, for example, liquid or semi-liquid preparations suitable for penetration through the skin (e.g., liniments, lotions, ointments, creams, or pastes). Other modes of administration are known in the art and are encompassed by the embodiments described herein.

A better understanding of the present invention and of its many advantages will be gained from the following examples, given by way of illustration.

EXAMPLES

Example 1

Cell-Free Solution of Mupirocin Acid in Water

A fermentation broth containing mupirocin acid was obtained by fermenting a mupirocin producing culture of *Pseudomonas fluorescens* in a manner known per se, i.e. in line with the procedure of example 1 in U.S. Pat. No. 3,977,943. Five liters mupirocin-containing whole culture fermentation broth from a laboratory fermentor was adjusted to pH=8.3 (by addition of 3M NaOH) and filtered through a 144 μm metal screen at room temperature, followed by ultrafiltration (Millipore Pellicon-2 Biomax-5). About 70% of the mupirocin present in the fermentation broth was recovered in the final clarified broth. Optionally, the mupirocin containing permeate was concentrated by NF (Osmonic Desal DK membrane).

Example 2

Adsorption of Pseudomonic Acid to a Solid Support and Conversion to Mupirocin Calcium A. A filtrate obtained as in Example 1 (363 ml, 1.3 g mupirocin) was added $(NH_4)_2SO_4$ (24 g). The pH was adjusted to pH 7.5 by addition of 1 M NaOH. The acrylic adsorbent XAD7HP® (Rohm & Haas) was packed into a chromatography column (24 ml) and the prepared mupirocin solution (in the form of pseudomonate solution) was added to the column (1 ml/min). The column was washed with 0.1M Tris-buffer containing 0.5M $(NH_4)_2SO_4$, pH 7.5 (120 ml). A 0.1M calcium acetate solution was then added to the column (72 ml), followed by water (48 ml). Mupirocin calcium was eluted from the column with 80% methanol. 0.9 g mupirocin calcium was recovered in the elution pool (60 ml, 70% yield).

B. A filtrate obtained as in Example 1 (293 ml, 1.5 g mupirocin), was added $(NH_4)_2SO_4$ (19 g). The pH was adjusted to pH 7.5 by addition of 1M NaOH. The polystyrene divinylbenzene adsorbent XAD1600® (Rohm & Haas) was packed into a chromatography column (22 ml) and the prepared mupirocin solution (in the form of pseudomonate solution) was added to the column (1 ml/min). The column was washed with a 0.1M Tris-buffer containing 0.5M $(NH_4)_2SO_4$, pH 7.5 (110 ml). A 0.1M calcium acetate solution was subsequently added to the column (66 ml), followed by water (66 ml). Mupirocin calcium was eluted from the column with 80% methanol. 1.3 g mupirocin calcium was recovered in the elution pool (55 ml, 87% yield).

C. A filtrate obtained as in Example 1 (1035 ml, 5.8 g mupirocin), was added $(NH_4)_2SO_4$ (68 g). The pH was adjusted to pH 7.5 by addition of 1M NaOH. The acrylic adsorbent XAD7HP® (Rohm & Haas) was packed into a chromatography column (191 mL) and the prepared mupirocin solution (in the form of pseudomonate solution) was added to the column (1.9 ml/min). The column was washed with 0.1M Tris-buffer containing 0.5M $(NH_4)_2SO_4$, pH 7.5 (958 ml). A 0.1M calcium acetate solution was added to the column (575 ml), followed by water (573 ml). Mupirocin calcium was eluted from the column with 60% methanol. 5.0 g mupirocin calcium was recovered in the elution pool (216 ml, 83% yield).

A fraction of the elution pool (54 ml, 1.2 g mupirocin calcium) was evaporated (90 mbar, 50° C.). The resulting methanol free solution (15 ml) was allowed to crystallize with stirring at room temperature. After approximately 20 hr the crystalline material was filtered off and the resulting filter cake was washed with water (10 ml) and dried in a vacuum tray dryer (<50 mbar, 40° C.). 1.1 g product was recovered with a specific activity of 91.4% ('as is').

D. Purified mupirocin acid (10 g, containing 94% active substance) was dissolved in a 0.5M $(NH_4)_2SO_4$-solution (1 L). The solution was adjusted to pH 7.5 with 1M NaOH. The polystyrene divinyl benzene adsorbent XAD4® (Rohm & Haas) was packed into a chromatography column (22 mL) and the prepared mupirocin solution (in the form of pseudomonate solution) was added to the column (88 ml, 2 ml/min). The column was washed with 0.1M phosphate-buffer pH 7.5 containing 0.5M $(NH_4)_2SO_4$ (33 ml), followed by 0.1M phosphate-buffer, pH 7.5 (110 ml), and finally water (66 ml). A 0.1M $CaCl_2$ solution was added to the column (66 ml). Surplus of calcium was washed out by water (66 ml), followed by 20% methanol (176 ml). Mupirocin calcium was eluted from the column with 60% methanol (176 ml). 0.5 g mupirocin calcium was recovered in the elution pool (121 ml, 51% yield).

The eluted product was evaporated under vacuum in a laboratory rotary evaporator (80 mbar, 50° C.). The concentrated and methanol free solution (2.5 ml) was allowed to crystallize with stirring at room temperature. After 20 hr the crystalline material was filtered off, and the filter cake was dried in a tray vacuum dryer (<50 mbar, 50° C.). 0.3 g product was recovered with a specific activity of 92% ('as is') and melting point of 125° C. The FT-IR spectrum for the product corresponds to the reference spectrum for mupirocin calcium.

While the present invention has been described in terms of the preferred embodiments, it is understood that variations and modifications will occur to those skilled in the art. Therefore, it is intended that the appended claims cover all such equivalent variations that come within the scope of the invention as claimed.

The invention claimed is:

1. A method for purifying mupirocin calcium comprising adsorbing a preparation of mupirocin to a hydrophobic solid support to produce bound mupirocin, exposing the bound mupirocin to a soluble calcium-containing agent to produce mupirocin calcium, washing the bound mupirocin calcium, and eluting purified mupirocin calcium from the solid support.

2. The method of claim 1 wherein the preparation of mupirocin is prepared by fermenting a mupirocin-producing culture of *Pseudomonas fluorescens*, obtaining the fermentation broth produced thereby, and optionally clarifying the broth by filtration.

3. The method of claim 1 wherein the solid support is a hydrophobic adsorbent resin.

4. The method of claim 3 wherein the resin comprises modified silica, a polystyrene or an acrylic material.

5. The method of claim 4 wherein the resin comprises acrylic adsorbent XAD7HP, or the polystyrene divinylbenzene adsorbents XAD1600 or XAD4.

6. The method of claim 1 wherein the mupirocin calcium is further purified by crystallization.

7. The method of claim 1 wherein the mupirocin calcium is purified to at least 50%.

8. The method of claim 1 wherein the mupirocin calcium is purified to at least 65%.

9. The method of claim 1 wherein the mupirocin calcium is purified to at least 90%.

10. The method of claim 1 wherein a base is added to the preparation of mupirocin to aid adsorption to the solid support.

11. The method of claim 1 wherein the calcium-containing agent comprises calcium acetate, calcium chloride, calcium nitrate or calcium propionate.

12. The method of claim 1 wherein the preparation of mupirocin is in the form of pseudomonate, ammonium sulfate solution is added to the preparation of mupirocin to aid adsorption of the mupirocin to the solid support, the solid support is the acrylic adsorbent XAD7HP or the polystyrene divinylbenzene adsorbent XAD 1600, the calcium containing agent is calcium acetate, and the purified mupirocin calcium is eluted using an organic solvent.

13. The method of claim 1 wherein the preparation of mupirocin is in the form of mupirocin acid, ammonium sulfate solution is added to the preparation of mupirocin to aid adsorption of the mupirocin to the solid support, the solid support is the polystyrene divinylbenzene adsorbent XAD4, the calcium-containing agent is calcium chloride and the purified mupirocin calcium is eluted using an organic solvent.

14. The method of claim 11 wherein the calcium-containing solution comprises calcium acetate.

15. The method of claim 11 wherein the calcium-containing solution comprises calcium chloride.

16. The method of claim 1 wherein mupirocin calcium is eluted from the solid support using an organic solvent.

17. The method of claim 16 wherein the organic solvent comprises methanol.

18. The method of claim 1 wherein the mupirocin is in the form of pseudomonate, ammonium sulfate solution is added to the mupirocin to aid adsorption of the mupirocin to the solid support, the solid support is the acrylic adsorbent XAD7HP or the polystyrene divinylbenzene adsorbent XAD 1600 and the mupirocin calcium is eluted using an organic solvent.

19. The method of claim 1 wherein the mupirocin is in the form of mupirocin acid, ammonium sulfate solution is added to the mupirocin to aid adsorption of the mupirocin to the solid support, the solid support is the polystyrene divinylbenzene adsorbent XAD4, the calcium-containing solution is calcium chloride and the mupirocin calcium is eluted using an organic solvent.

\* \* \* \* \*